(12) United States Patent
Kuhn

(10) Patent No.: US 9,999,789 B2
(45) Date of Patent: Jun. 19, 2018

(54) TEMPERATURE DISTRIBUTION DETERMINING APPARATUS

(75) Inventor: Michael Harald Kuhn, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1341 days.

(21) Appl. No.: 13/697,823

(22) PCT Filed: May 9, 2011

(86) PCT No.: PCT/IB2011/052029
§ 371 (c)(1),
(2), (4) Date: Nov. 14, 2012

(87) PCT Pub. No.: WO2011/145020
PCT Pub. Date: Nov. 24, 2011

(65) Prior Publication Data
US 2013/0060243 A1   Mar. 7, 2013

(30) Foreign Application Priority Data
May 17, 2010   (EP) .................................... 10162922

(51) Int. Cl.
*A61B 18/00* (2006.01)
*A61B 8/08* (2006.01)
(Continued)

(52) U.S. Cl.
CPC ............... *A61N 7/00* (2013.01); *A61B 5/015* (2013.01); *A61B 8/48* (2013.01); *A61B 18/00* (2013.01);
(Continued)

(58) Field of Classification Search
USPC ............................................ 600/439; 606/27
See application file for complete search history.

(56) References Cited

U.S. PATENT DOCUMENTS 6,086,535 A   7/2000   Ishibashi et al.
6,823,216 B1   11/2004   Salomir et al.
(Continued)

FOREIGN PATENT DOCUMENTS

JP   1997103434 A   4/1997
JP   2003035607 A   2/2003
(Continued)

OTHER PUBLICATIONS

Gomez et al. "Spatial estimation of mean temperature and precipitation in areas of scarce meteorological information", Atmosfera, No. 21, Vo. 1, pp. 35-56 , 2008.*
(Continued)

*Primary Examiner* — Katherine Fernandez
*Assistant Examiner* — Marjan Saboktakin

(57) ABSTRACT

The invention relates to a temperature distribution determining apparatus for determining a temperature distribution within an object caused by applying energy to the object. A temperature distribution measuring unit (6, 7) measures a spatially and temporally dependent first temperature distribution in the object (3), while the energy is applied to the object (3) such that the object (3) is heated to a temperature within a first temperature range, and a temperature distribution estimating unit (5) estimates a spatially and temporally dependent second temperature distribution in the object (3) within a second temperature range, which is different to the first temperature range, based on the spatial and temporal dependence of the measured first temperature distribution. Since temperature distributions can be obtained not only in the first temperature range, but also in the second temperature range, the overall temperature range, in which the temperature distribution can be determined, can be increased.

13 Claims, 4 Drawing Sheets

(51) Int. Cl.
*A61N 7/00* (2006.01)
*A61B 18/12* (2006.01)
*A61B 5/01* (2006.01)
*G01K 11/24* (2006.01)
*G01K 13/00* (2006.01)
*A61B 8/00* (2006.01)
*A61B 17/00* (2006.01)
*A61B 8/06* (2006.01)

(52) U.S. Cl.
CPC ......... *A61B 18/1206* (2013.01); *G01K 11/24* (2013.01); *G01K 13/002* (2013.01); *A61B 8/06* (2013.01); *A61B 8/085* (2013.01); *A61B 8/463* (2013.01); *A61B 8/469* (2013.01); *A61B 8/483* (2013.01); *A61B 8/485* (2013.01); *A61B 8/488* (2013.01); *A61B 8/5261* (2013.01); *A61B 8/58* (2013.01); *A61B 2017/00084* (2013.01); *A61B 2018/00803* (2013.01); *A61B 2562/0204* (2013.01); *G01K 2213/00* (2013.01)

(56) References Cited

U.S. PATENT DOCUMENTS

| | | | |
|---|---|---|---|
| 2006/0184163 A1* | 8/2006 | Breen | A61B 18/04 606/20 |
| 2007/0106157 A1 | 5/2007 | Kaczkowski et al. | |
| 2009/0312637 A1 | 12/2009 | Raju et al. | |
| 2009/0326420 A1 | 12/2009 | Moonen et al. | |
| 2010/0036378 A1* | 2/2010 | Savery | A61B 18/1206 606/42 |
| 2011/0313329 A1 | 12/2011 | Kohler et al. | |

FOREIGN PATENT DOCUMENTS

| | | | | |
|---|---|---|---|---|
| WO | 2006001806 A2 | | 1/2006 | |
| WO | WO2008091655 | | 7/2008 | |
| WO | WO 2010/029479 | * | 3/2010 | ............... A61N 7/02 |
| WO | WO-2011/091847 | * | 8/2011 | ............... A61B 5/00 |

OTHER PUBLICATIONS

Anand, A. et al. "P2H-3 Ultrasonic Spatial and Temporal Determination of Heat Deposition in Three Dimensions", Ultrasonics Symposium, 2006. IEEE, Oct. 2-6, 2006, pp. 1758-1761.
Varghese, T. et al. "Ultrasound monitoring of temperature change during radiofrequency ablation: preliminary in-vivo results", Ultrasound in Medicine & Biology, vol. 28, Issue 3, Mar. 2002, pp. 321-329.
A. Vanne et al., "MRI Feedback Temperatur Control for Focused Ultrasound Surgery", Institute of Physics Publishing, Phys. Med. Biol. 48 (2003), pp. 31-43.
A. Anand et al., "Three-Dimensional Spatial and Temporal Temperature Imaging in Gel Phantoms Using Backscattered Ultrasound", IEEE Transactions on Ultrasonics, Ferroelectrics, and Frequency Control, vol. 54, No. 1, Jan. 1, 2007, pp. 23-31.
C. Hanson et al., "Interactive Determination of Robust Safety Margins for Oncologic Liver Surgery", one page.

* cited by examiner

TEMPERATURE DISTRIBUTION DETERMINING APPARATUS

FIELD OF THE INVENTION

The invention relates to a temperature distribution determining apparatus and method for determining a temperature distribution within an object caused by applying energy to the object. The invention relates further to a corresponding computer program for determining a temperature distribution within an object caused by applying energy to the object.

BACKGROUND OF THE INVENTION

An apparatus for ultrasound-based temperature imaging is disclosed in the article "Three-dimensional spatial and temporal temperature imaging in gel phantoms using backscattered ultrasound" by Ajay Anand et al., IEEE Transactions on Ultrasonics, Ferreoelectrics, and Frequency Control, vol. 54, no. 1, pages 23-31 (January 2007). Ultrasound data are acquired from a gel phantom by using backscattered ultrasound, and a three-dimensional spatial and temporal ultrasound temperature distribution is determined from the acquired ultrasound data. The apparatus can measure the temperature distribution only within a temperature range below 55° C., i.e. the apparatus is not able to determine a three-dimensional spatial and temporal ultrasound temperature distribution within, for example, a therapeutic ablation temperature range of about 55 to 60° C.

SUMMARY OF THE INVENTION

It is an object of the present invention to provide a temperature distribution determining apparatus for determining a temperature distribution within an object caused by applying energy to the object, wherein the temperature range, in which the temperature distribution can be determined, can be increased.

In a first aspect of the present invention a temperature distribution determining apparatus for determining a temperature distribution within an object caused by applying energy to the object is presented, wherein the temperature distribution determining apparatus comprises:

a temperature distribution measuring unit for measuring a spatially and temporally dependent first temperature distribution in the object, while the energy is applied to the object such that the object is heated to a temperature within a first temperature range, a temperature distribution estimating unit for estimating a spatially and temporally dependent second temperature distribution in the object within a second temperature range, which is different to the first temperature range and in which the temperature distribution measuring unit cannot measure a temperature distribution, based on the spatial and temporal dependence of the measured first temperature distribution.

Since the temperature distribution estimating unit estimates a spatially and temporally dependent second temperature distribution in the object within a second temperature range, which is different to the first temperature range and in which the temperature distribution measuring unit cannot measure a temperature distribution, the temperature range, in which the temperature distribution can be determined, can be increased, and the apparatus can therefore be used, for example, for monitoring a three-dimensional spatial and temporal temperature distribution over an enlarged temperature range, in particular, during a therapeutical ablation procedure like a procedure for ablating a pathologal lesion or a complete organ of a person.

It is preferred that the temperature distribution measuring unit comprises an ultrasound unit for acquiring ultrasound data from the object and a temperature distribution calculation unit for calculating the first temperature distribution depending on the acquired ultrasound data. The use of an ultrasound unit allows acquiring data of the object in a relatively simple way, for example, in comparison to using a magnetic resonance imaging system or a computed tomography imaging system for acquiring data of the object. Moreover, an ultrasound unit is portable, such that it can be used by, for example, a private physician, and, by determining a temperature distribution based on ultrasound data, the temperature distribution can be determined with high accuracy.

The temperature distribution measuring unit is preferentially adapted to measure a two- or three-dimensional first temperature distribution, and the temperature distribution estimating unit is preferentially adapted to estimate a two- or three-dimensional second temperature distribution, i.e. the first temperature distribution and the second temperature distribution preferentially have two or three spatial dimensions. The spatially and temporally dependent first temperature distribution is preferentially determined by measuring a spatial temperature distribution over time. Preferentially, the temperature distribution estimating unit is adapted to extrapolate the measured first temperature distribution from the first temperature range into the second temperature range for estimating the second temperature distribution. In an embodiment, it is assumed that the energy is applied to the object such that a temperature of the object is changed from a temperature within the first temperature range to a temperature within the second temperature range, wherein the temperature distribution estimating unit is adapted to extrapolate the measured first temperature distribution from time points, at which the object has a temperature within the first temperature range, to time points, at which the object has a temperature within the second temperature range. For example, the energy can be applied such that the temperature increases from about 37° C. to a value equal to or smaller than 50° C. or 55° C., in a time interval during which the first temperature distribution is measured over time. The first temperature distribution then describes a temporal and spatial evolution of the temperature within the object in the first temperature range. The temperature distribution estimating unit is preferentially adapted to estimate the second temperature distribution, in particular, to extrapolate the second temperature distribution in time and space, based on the measured temporal and spatial evolution of the temperature within the first temperature range. The temperature distribution estimating unit can be adapted to use heat-diffusion equations and possibly known parameters of the object like local heat-diffusion coefficients, in particular, a three-dimensional distribution of the heat diffusion coefficients in the object.

The temperature distribution determining apparatus can comprise an energy application characteristics providing unit for providing energy application characteristics describing the application of energy to the object such that the object is heated to a temperature within the second temperature range. Moreover, the temperature distribution estimating unit can be adapted to estimate the spatially and temporally dependent second temperature distribution in the object within the second temperature range based on the spatial and temporal dependence of the measured first temperature distribution and the provided energy application characteristics.

The temperature distribution determining apparatus is preferentially adapted to determine a temperature distribution within an organ of a person like the heart, the kidney, the liver et cetera, wherein the energy is applied within the person by using a catheter. For example, the energy can be applied for performing an ablation procedure or any other form of thermal initiation of treatment at temperatures above 55° C., such as thermal drug release or genetic therapy, on or within the organ.

In the ablation case, the energy is preferentially applied to induce cell death within a part of a living object like an organ of a person by coagulation. The second temperature range can therefore be regarded as a therapeutic ablation temperature range and is preferentially above 55° C., further preferred above 60° C. The energy is preferentially applied to perform a thermal ablation on a pathology within an organ of a person like the heart or the liver. The temperature distribution estimating unit is therefore preferentially adapted to estimate the second temperature distribution as it is created during thermal ablation in a second temperature range above 55° C. or above 60° C. The first temperature range is, for example, below a temperature of 50° C.

The temperature distribution determining apparatus can be adapted to measure the first temperature distribution and estimate the second temperature distribution in the same area of the object or in separate areas of the object. The separate areas can be overlapping or non-overlapping areas. In particular, the areas can be adjacent non-overlapping areas. If a first area, in which the first temperature distribution is measured, is different to a second area, in which the second temperature distribution is estimated, the first temperature distribution is preferably spatially extrapolated from the first area to the second area, wherein the first temperature distribution is also temporally extrapolated, for estimating the second temperature distribution in the second area.

The temperature distribution determining apparatus preferentially further comprises an energy application characteristics providing unit for providing energy application characteristics describing the application of energy to the object such that the object is heated to a temperature up to values within the second temperature range, at which the second temperature distribution should be estimated. Preferentially, the energy application characteristics providing unit is adapted to provide energy application characteristics of applying RF energy to the object. Energy application characteristics of applying RF energy are, for example, the structure of one or several RF electrodes used for applying the RF energy to the object, the location of the one or several RF electrodes with respect to the object, the power applied to the object via the one or several RF electrodes, the temporal pattern in which the power is applied to the object, et cetera. By using RF energy, heat can be generated locally at locations, at which one or several RF electrodes are placed, with high accuracy. However, the energy application characteristics providing unit can also be adapted to provide energy application characteristics of other kinds of energy like another kind of electrical energy like microwaves, optical energy, ultrasound energy, nuclear energy, et cetera. The provided energy application characteristics can be initially provided energy application characteristics, or modified provided energy application characteristics.

It is preferred that the temperature distribution determining apparatus further comprises an estimated influence region determining unit for determining an estimated influence region of the object depending on the estimated second temperature distribution, wherein the estimated influence region is indicative of the region of the object, in which the object is influenced to a predefined degree by the application of energy. For example, a temperature threshold can be defined, wherein parts of the object having, regarding the second temperature distribution, a temperature above the temperature threshold form the estimated influence region. The temperature threshold is preferentially equal to or larger than 60° C.

It is further preferred that the temperature distribution determining apparatus comprises:

an energy application characteristics providing unit for providing energy application characteristics describing the application of energy to the object such that the object is heated to a temperature within the first temperature range, while the temperature distribution measuring unit measures the first temperature distribution, and further to a temperature within the second temperature range, an influenced deviation determining unit for determining a deviation between the estimated influence region and a predefined influence region, an energy application characteristics adaption unit for adapting the provided energy application characteristics depending on the determined deviation. The predefined influence region is preferentially a previously planned and/or desired influence region. For example, an image of the object like a magnetic resonance image or a computed tomography image can be provided, wherein the image shows a region, in which, for example, a tumor is located and to which energy should be applied. A user can then mark this region in the image for providing a predefined influence region. The marking of the region for predefining the influence region can also be performed automatically, wherein preferentially a user can modify the automatically predefined influence region. While the energy is applied to the object in accordance with the provided energy application characteristics and while the temperature of the object increases within the first temperature range, the temperature distribution measuring unit measures a spatially and temporally dependent first temperature distribution in the object. Based on the temporal and spatial evolution of the first temperature distribution, i.e. based on the spatial and temporal dependence of the measured first temperature distribution, a spatially and temporally dependent second temperature distribution within the second temperature range is estimated, preferentially without heating the object to a temperature within the second temperature range. Then, the estimated influence region determining unit determines an estimated influence region of the object depending on the estimated second temperature distribution. Since the energy application characteristics adaptation unit is configured for adapting the provided energy application characteristics depending on the determined deviation between the estimated influence region and the predefined influence region, the application of energy can be corrected such that the finally influenced region will better match the predefined influence region. For instance, the energy application characteristics adaptation unit can be adapted to amend the provided energy application characteristics depending on the determined deviation, wherein then the second temperature distribution and the estimated influence region are calculated again on the basis of the adapted energy application characteristics. This can be performed until the deviation between the actually estimated influence region and the predefined influence region is below a predefined threshold or until a predefined number of iterations has been performed. Preferentially, before energy is applied to the object in accordance with the adapted energy application characteristics, the estimated influence region is shown to a user and the user has to agree with the estimated influence region, before the energy is applied. For example, the estimated influence region can be shown on a display and the temperature distribution determining apparatus comprises an input device like a keyboard or a mouse, wherein energy is applied to the object only, if the user has entered that he/she agrees with the estimated influence region.

It is preferred that the temperature distribution determining apparatus further comprises a display for showing an overlay image of the estimated influence region and a predefined influence region. This allows a user to readily recognize whether the energy application characteristics, which are intended to be applied to the object, yield a desired effect, i.e. the degree of matching the predefined influence region by the estimated influence region can readily be seen.

It is further preferred that the temperature distribution determining apparatus comprises an energy application characteristics providing unit for providing energy application characteristics describing the application of energy to the object such that the object is heated to a temperature within the second temperature range, wherein the energy application characteristics providing unit is adapted for allowing a user to modify the provided energy application characteristics, wherein the temperature distribution estimating unit is adapted for estimating a modified second temperature distribution in the object within the second temperature range, which would be present, if the energy would be applied to the object in accordance with the modified provided energy application characteristics, wherein the estimated influence region determining unit is adapted for determining a modified estimated influence region of the object depending on the estimated modified second temperature distribution. For example, the temperature distribution measuring unit can measure a spatially and temporally dependent first temperature distribution in the object, while the energy is applied to the object in accordance with the modified provided energy application characteristics and while the temperature of the object increases within the first temperature range. The temperature distribution estimating unit can then estimate the modified second temperature distribution based on the temporal and spatial evolution of the measured first temperature distribution, i.e. based on the spatial and temporal dependence of the measured first temperature distribution. If a user does not agree with the modified estimated influence region, which has been determined based on the estimated modified second temperature distribution, energy is preferentially not applied in accordance with the modified provided energy application characteristic such that the object is not heated to a temperature within the second temperature range, and, if the user agrees with the modified estimated influence region, the energy is preferentially applied in accordance with the modified provided energy application characteristics for heating the object to a temperature within the second temperature range. The temperature distribution determining apparatus comprises preferentially an input unit allowing the user to enter that he/she agrees or does not agree with the modified estimated influence region. If the user does not agree with the modified estimated influence region, the user might modify the energy application characteristics again.

It is further preferred that temperature distribution determining apparatus comprises an energy application characteristics providing unit for providing energy application characteristics describing the application of energy to the object such that the object is heated to a temperature within the second temperature range, wherein the temperature distribution measuring unit is adapted for measuring a third temperature distribution in the object in the first temperature range in a first part of the object, while the energy is applied to the object in accordance with the provided energy application characteristics, if the first part of the object has a temperature within the first temperature range and a second part of the object has a temperature within the second temperature range, wherein the temperature distribution estimating unit is adapted for estimating a fourth temperature distribution in the second part of the object within the second temperature range, which is present while the energy is applied to the object in accordance with the provided applied energy application characteristics, based on at least one of: the measured first temperature distribution, the estimated second temperature distribution and the measured third temperature distribution, in particular, by spatially and/or temporally extrapolating at least one of the measured first temperature distribution, the estimated second temperature distribution and the measured third temperature distribution into a spatial and/or temporal region, respectively, which corresponds to the fourth temperature range. If several fourth temperature distributions have been determined by extrapolating at least two of the measured first temperature distribution, the estimated second temperature distribution and the measured third temperature distribution, these several fourth temperature distributions can be averaged for obtaining a single fourth temperature distribution. The estimated influence region determining unit can then be adapted to determine the estimated influence region of the object depending on the estimated fourth temperature distribution. Moreover, the influenced deviation determining unit can be adapted to determine a deviation between the estimated influence region, which has been estimated depending on the fourth temperature distribution, and the predefined influence region, wherein the energy application characteristics adaption unit is configured to adapt the energy application characteristics, which describe the current application of energy to the object, depending on the determined deviation. Thus, even during the application of energy the temperature distribution can be determined and the application of energy can be adapted in accordance with the determined temperature distribution. This can further decrease deviations between a finally influenced region of the object and the predefined influence region.

It is further preferred that the temperature distribution determining apparatus comprises an energy application characteristics providing unit for providing energy application characteristics describing the application of energy to the object such that the object is heated to a temperature within the second temperature range, and an energy application unit for applying the energy to the object in accordance with the provided energy application characteristics. The energy application unit is preferentially adapted to apply energy in accordance with initially provided energy application characteristics and/or modified provided energy application characteristics. The temperature distribution determining apparatus can therefore also be regarded as the core part of a control unit of an energy application apparatus for applying energy to an object, or the temperature distribution determining apparatus can be regarded as the energy application apparatus itself.

It is further preferred that the temperature distribution measuring unit is adapted for measuring several first temperature distributions in the object, while the energy is applied to the object in accordance with several measurement energy application characteristics such that the object is heated to different temperatures within the first temperature range, wherein the temperature distribution determining apparatus comprises an energy application characteristics providing unit for providing energy application characteristics describing the application of energy to the object such that the object is heated to a temperature within the second temperature range, and wherein the temperature distribution estimating unit is adapted for estimating the second temperature distribution by extrapolating the several measured first temperature distributions from the several measurement energy application characteristics to the provided energy application characteristics. The extrapolation allows to determine the second temperature distribution with relatively low computational efforts.

It is preferred that the temperature distribution determining apparatus further comprises an object structure providing unit for providing a structure of the object, wherein the temperature distribution estimating unit is adapted to estimate the second temperature distribution based on the provided structure of the object. Also the fourth temperature distribution can be estimated based on the provided structure of the object. For example, if the object is an organ, the provided structure can show positions of blood vessels which cool the object and influence the temperature distribution. The structure can be provided as a segmented image of the object. The temperature distribution estimating unit can be adapted to use heat-diffusion equations and possibly known parameters of the object like heat-diffusion coefficients. The heat-diffusion coefficients are general material specific. If the structure shows different materials in different regions of the object, a spatial distribution of heat-diffusion coefficients can be defined. The spatial distribution of heat-diffusion coefficients is preferentially used for estimating the temperature distribution by extrapolation by using the heat-diffusion equations. The temperature distribution estimating unit can further be adapted to estimate the second temperature distribution based on the blood flow velocity within blood vessels. The blood flow velocity can be determined based on, for example, ultrasound data acquired by the ultrasound unit of the temperature distribution measuring unit, in particular, by using the known ultrasound Doppler effect. The ultrasound unit can therefore be used for acquiring ultrasound data for at least two purposes, measuring the first temperature distribution within the first temperature range and determining the blood flow velocity within a blood vessel. The ultrasound data can further be used for guiding purposes for guiding energy application elements like ablation electrodes to a desired location within the object.

It is preferred that the temperature distribution determining apparatus further comprises an influenced region determining unit for determining an influenced region being indicative of the region of the object, in which the object has been influenced to a predefined degree by the application of energy. For example, the influenced region determining unit can be adapted to use ultrasound elastography for determining the influenced region. This allows a user to assess the quality of the performed energy application procedure, in particular, by comparing the influenced region with the predefined influence region.

In a further aspect of the present invention a temperature distribution determining method for determining a temperature distribution within an object caused by applying energy to the object is presented, wherein the temperature distribution determining method comprises:

measuring a spatially and temporally dependent first temperature distribution in the object, while the energy is applied to the object such that the object is heated to a temperature within a first temperature range, by a temperature distribution measuring unit, estimating a spatially and temporally dependent second temperature distribution in the object within a second temperature range, which is different to the first temperature range and in which the temperature distribution measuring unit cannot measure a temperature distribution, based on the spatial and temporal dependence of the measured first temperature distribution.

In a further aspect of the present invention a computer program for determining a temperature distribution within an object caused by applying energy to the object is presented, wherein the computer program comprises program code means for causing a temperature distribution determining apparatus as defined in claim 1 to carry out the steps of the temperature distribution method as defined in claim 14, when the computer program is run on a computer controlling the temperature distribution determining apparatus.

It shall be understood that the temperature distribution determining apparatus of claim 1, the temperature distribution determining method of claim 14 and the computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
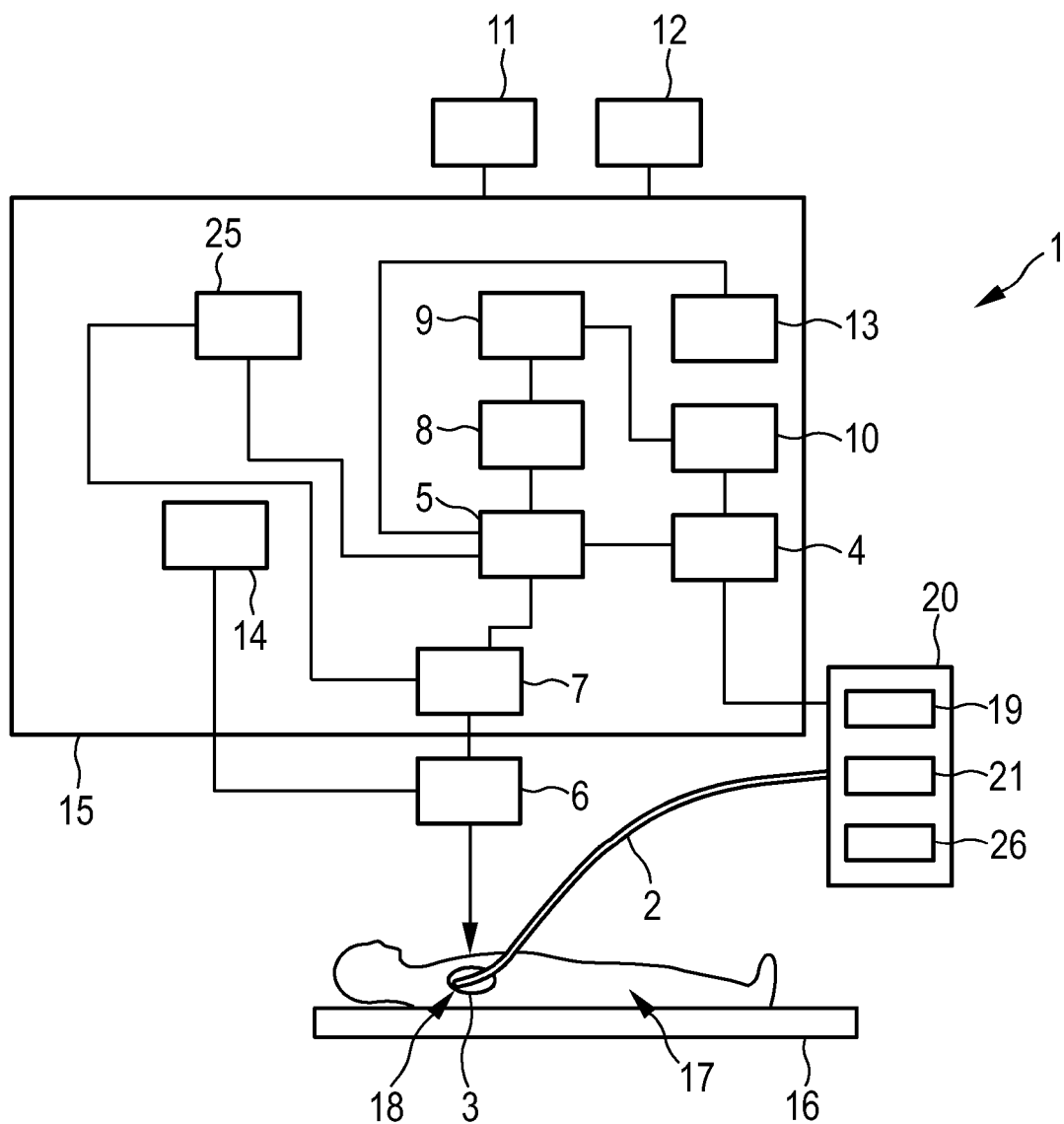
FIG. 1 shows schematically and exemplarily an embodiment of a temperature distribution determining apparatus for determining a temperature distribution within an object caused by applying energy to the object.

FIG. 1 shows schematically and exemplarily a temperature distribution determining apparatus 1 for determining a temperature distribution within an object 3 caused by applying energy to the object 3. In this embodiment, the object 3 is an organ of a person 17 located on a table 16. The organ 3 is, for example, the heart, the liver, one of the kidneys, et cetera. An influence region within the object 3 has been predefined. For example, a physician has marked the influence region in an image of the object 3 for predefining the influence region. The predefined influence region can mark a lesion like a tumor within the object 3. The image can be provided during a prior measurement performed by an imaging modality like a magnetic resonance imaging system, a computed tomography imaging system, a nuclear imaging system, an ultrasound imaging system, et cetera.

The temperature distribution determining apparatus 1 comprises a catheter 2 with a catheter tip 18 which is arranged at, in particular, within, the predefined influence region. However, the temperature distribution determining apparatus can also comprise a needle-like device with a needle tip. The catheter tip 18 is schematically and exemplarily shown in more detail in FIGS. 2 to 4.

Figure 2:
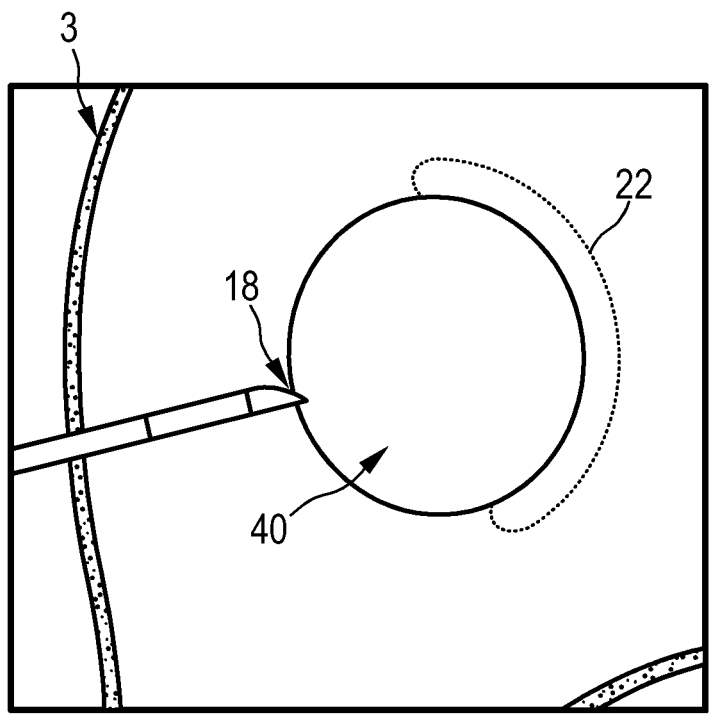
FIGS. 2 to 4 show schematically and exemplarily a catheter tip comprising ablation electrodes for applying ablation energy to the object.
Figure 3:
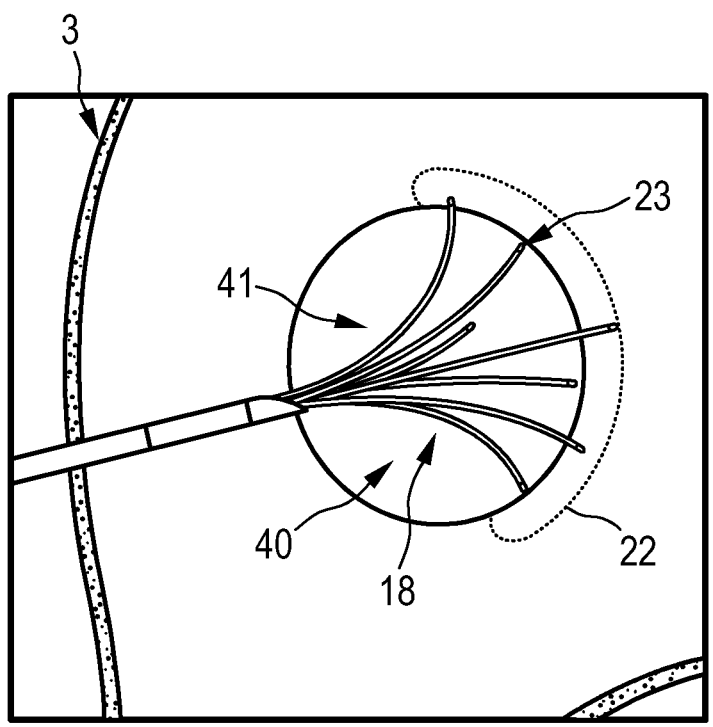

FIG. 2 shows a situation in which the catheter tip 18 has been introduced into the organ 3 such that it reaches a cavity 40 with a predefined influence region 22. While forwarding the catheter tip 18 from outside the person 17 to the cavity 40 sub tips 41 with ablation electrodes 23 are located within the catheter tip 18. After the cavity 40 has been reached, the sub tips 41 with the ablation electrodes 23 are moved out of the catheter tip 18, wherein the sub tips 41 bend into different directions for applying electrical energy at different locations (FIG. 3). In this embodiment, the ablation electrodes are RF electrodes which are electrically connected with an RF energy source 20 via electrical connections within the catheter 2. The ablation electrodes 23 form together with the RF energy source 20 and the electrical connections for connecting the ablation electrodes and the RF energy source an energy application unit for applying energy to the object 3.

The temperature distribution determining apparatus 1 further comprises a temperature distribution measuring unit for measuring a first temperature distribution in the object 3, while the ablation energy is applied to the object 3 such that the object 3 is heated to a temperature within a first temperature range. The temperature distribution measuring unit comprises an ultrasound unit 6 for acquiring ultrasound data from the object 3 and a temperature distribution calculation unit 7 for calculating the first temperature distribution depending on the acquired ultrasound data.

The temperature distribution measuring unit measures a three-dimensional first temperature distribution, which is a spatial temperature distribution, over time. The RF energy is applied such that the temperature increases from about 37° C. to a value of about 50° C. or 55° C., while the first temperature distribution is measured over time. The first temperature distribution describes therefore a temporal and spatial evolution of the temperature within the object in the first temperature range being, in this embodiment, from about 37° C. to about 50° C. or 55° C. In other embodiments, the first temperature range can be smaller, for example, it can range from about 37° C. to a temperature being smaller than 50° C. The first temperature range is chosen such that it provides enough temperature data for estimating a second temperature distribution in the object within a second temperature range, which will be described further below.

The ultrasound unit 6 is in contact with the person 17 for acquiring the ultrasound data. The ultrasound unit 6 is preferentially located as close as possible to the predefined influence region on the outer surface of the person 17. The ultrasound unit 6 can be a real-time, two-dimensional ultrasound array probe for acquiring two-dimensional ultrasound data, in particular, for acquiring two-dimensional ultrasound B-mode images. Apparent spatial displacements within the object caused by variations in the speed of sound due to variations in the temperature are detected from the ultrasound data, and the temperature distribution is determined from these detected apparent spatial displacements. A corresponding relation between temperature changes and apparent spatial displacements can be determined by calibration measurements and these determined relations can then be used by the temperature distribution calculation unit 7 for calculating the first temperature distribution based on the apparent spatial displacements. A more detailed description of this known method for determining a temperature distribution based on ultrasound data is disclosed in the above mentioned article by Ajay Anand et al., which is herewith incorporated by reference. Also other known methods for measuring a three-dimensional temperature distribution based on two-dimensional or three-dimensional ultrasound data can be used for measuring the first temperature distribution over time.

In an embodiment, the electrode power is switched on by using the RF energy source 20 until a temperature of 55° C. has been reached in the predefined influence region or a part of it. This temperature is below the threshold of permanent cell damage. During heating the tissue, the three-dimensional first temperature distribution is continuously measured using the above described ultrasound thermometry method performed by the temperature distribution measuring unit. This phase, which can be regarded as a first phase, is preferentially only used for acquiring the first temperature distribution data, and after the critical temperature of 55° C. has been reached in the predefined influence region or part of it, the power is switched off and a following second phase can be started, in which the second temperature distribution is estimated.

The temperature distribution determining apparatus 1 further comprises an energy application characteristics providing unit 4 for providing energy application characteristics describing the application of energy to the object 3 such that the object 3 is heated to a temperature within the second temperature range being different to the first temperature range. The second temperature range is preferentially chosen such that cell death is induced within the object 3 of the person 17 by coagulation. The second temperature range is therefore preferentially a therapeutic ablation temperature range, in which a thermal ablation procedure can be performed. The second temperature range is preferentially above 55° C. and further preferred above 60° C. The second temperature range can also be a single temperature, for example, 60° C., at which cell death is induced. The energy application unit 20, 23 is adapted to apply energy to the object 3 in accordance with the provided energy application characteristics. The temperature distribution determining apparatus 1 can therefore also be regarded as an energy application apparatus for applying energy to an object. The provided energy application characteristics, according to which the object 3 is heated, can be initially provided energy application characteristics or provided energy application characteristics which have been modified as will be described further below.

The energy application characteristics providing unit 4 is adapted to provide energy application characteristics of applying RF energy to the object 3. Energy application characteristics are, for example, the structure of the several ablation electrodes 23, their locations with respect to the object 3, the power applied to the object 3 via the ablation electrodes 23, et cetera. The energy application characteristics providing unit can be a storing unit, in which these characteristics are stored already, and/or it can be an adapted to allow a user to input the energy application characteristics. The temperature distribution determining apparatus 1 comprises an input unit 11 like a keyboard or a mouse, which can be used for inputting the energy application characteristics into the temperature distribution determining apparatus 1.

The temperature distribution determining apparatus 1 further comprises a temperature distribution estimating unit 5 for estimating a second temperature distribution in the object 3 within the second temperature range, which would be present, if the energy would be applied to the object 3 in accordance with the provided energy application characteristics, based on the measured first temperature distribution and optionally the provided energy application characteristics. Also the second temperature distribution is a three-dimensional spatial temperature distribution over time.

The temperature distribution determining apparatus 1 further comprises an object structure providing unit 13 for providing a structure of the object. The temperature distribution estimating unit 5 is adapted to estimate the second temperature distribution also based on the provided structure of the object. For example, the provided structure can show blood vessels which cool the object 3 and influence the temperature distribution, preferably including also information on blood flow velocity in the vessels, and different parts of the object comprising different materials. The structure is preferentially provided as a segmented image of the object, wherein the different segments describe, for example, blood vessels and further parts of the object comprising different materials. The temperature distribution estimating unit 5 is adapted to use heat-diffusion equations and known parameters of the object like heat-diffusion coefficients. The heat-diffusion coefficients are material specific. The structure, which shows different materials in different parts of the object, defines therefore a spatial distribution of heat-diffusion coefficients, which is used by the temperature distribution estimating unit 5 for estimating the second temperature distribution by extrapolating the temporal and spatial evolution within the first temperature range defined by the measured first temperature distribution over time into the second temperature range.

The temperature distribution determining apparatus further comprises an estimated influence region determining unit 8 for determining an estimated influenced region of the object 3 depending on the estimated second temperature distribution, wherein the estimated influence region is indicative of the region of the object 3, in which the object 3 is influenced to a predefined degree by the application of energy. In this embodiment, energy should be applied to the object 3 for inducing cell death by coagulation. The estimated influence region determining unit 8 is therefore preferentially adapted to determine the estimated influence region such that parts of the object 3, having, regarding the second temperature distribution, a temperature above a predefined temperature threshold, form the estimated influence region. The temperature threshold is preferentially defined such that a temperature above the temperature threshold induces cell death by coagulation. For example, the temperature threshold can be 60° C. or slightly smaller like 58° C. or 59° C.

Thus, in a second phase the estimated influence region, which can also be regarded as an ablation zone, which is expected to be actually achieved based on provided energy application characteristics, in particular on initially provided power level settings, will be predicted based on the three-dimensional temperature distribution evolution over time measured by the temperature distribution measuring unit in the first phase and based on the second temperature distribution which is preferentially determined by extrapolation by using heat-diffusion algorithms and by taking knowledge about the nature of the tissue into account. Knowledge about the nature of the tissue, i.e. information about the tissue to be ablated, are, for example, the already above mentioned tissue-specific heat-diffusion coefficients which may differ, for example, between muscle and fat tissue and the information about the blood vessels and the flow speed in these vessels, which lead to heat transport away from the ablation zone. This information can be a combination of literature knowledge about tissue with information about the local anatomy at and preferentially around the predefined influence region. The information about the local anatomy is preferentially based on the provided structure, i.e. segmented images from imaging modalities which allow to distinguish between soft tissue types such as a magnetic resonance imaging modality or a computed tomography imaging modality. The information about blood flow and vessel locations can be obtained via the ultrasound probe 6, when operated in Doppler mode. If the provided structure provides also information about blood vessels, the algorithm for estimating the second temperature distribution can consider their cooling effect, and damaging effects on the blood vessels can be predicted, which may have to be excepted for the sake of complete tumor volume coverage of the ablation volume, including a prediction of regions of the object, which may be left without intact blood supply as a consequence, as described in, for example, the article "Interactive determination of robust safety margins for oncologic liver surgery" by C. Hansen et al., Proceedings CARS 2009 Int. J. of Comp. Assisted Radiology and Surgery, Vol 4, Supplement 1, page 94 (June 2009), which is herewith incorporated by reference.

In an embodiment, the extrapolation of the observed first temperature distribution evolution over time from the first temperature range below 50° C. to the second temperature range up to 60° C. or higher can be performed as follows: Based on the observed ultrasound data, the rise of temperature as a function of time is determined for each volume element in the three-dimensional ultrasound data set comprising the object. Each individual function of temperature over time is then extrapolated via a quadratic or higher order extrapolation, in order to extend up into the second temperature range up to 60° C. and higher.

There may be volume elements, which have not experienced a significant temperature elevation while the temperature has been elevated to 50° C. in the high field areas of the energy-supplying electrode arrangement, because they are located at a too large distance from the electrodes. In that case, an alternative algorithm can be used for estimating the second temperature distribution, which will be described in the following.

From the observed first temperature distribution evolution over time from the first temperature range, temperature-iso-contours (surfaces in space) are computed. As these temperature-iso-contours propagate away from the high field areas of the electrodes, their propagation can be characterized by motion vector fields. Then their temporal evolution can be extrapolated by expanding the iso-contours along the motion vectors. If several electrodes are present, the iso-contours will start as islands and then grow together over time, this approach will create difficulties when they will start to overlap, but since only the iso-contours towards the boundary of the ablation zone are of interest, and since this boundary is located at some distance away from the electrode array, these effects do not need to be studied in detail in a first approximation extrapolation approach. They will lead to higher temperatures near the electrodes, where coagulation will be safely achieved, and even some burning can be tolerated. The iso-contour of interest is the one forming at the critical coagulation temperature. When this contour approaches the boundary of the ablation zone, it will have become a single, closed contour, which can then be inspected for agreement with the intended target ablation zone in order to see whether adjustments in the energy levels are required in order to modify its shape and make it conform better with the target region.

If heat-diffusion equations and heat-diffusion coefficients should be used for estimating the second temperature distribution, the temperature distribution estimating unit 5 can be adapted to use the following mathematical framework.

The heat-diffusion equation is an important partial differential equation which describes the distribution of heat (or variation in temperature) in a given region over time. For a function u(x,y,z,t) of three spatial variables (x,y,z) and the time variable t, the heat equation is $$\frac{\partial u}{\partial t} - \alpha \left( \frac{\partial^2 u}{\partial x^2} + \frac{\partial^2 u}{\partial y^2} + \frac{\partial^2 u}{\partial z^2} \right) = 0, \quad (1)$$

or equivalently $$\frac{\partial u}{\partial t} = \alpha \nabla^2 u \quad (2)$$

with $$\alpha = k/c_p \rho \quad (3)$$

The value α is a material-specific quantity depending on the thermal conductivity, k, the mass density, ρ, and the specific heat capacity, $c_p$. In the context of this invention, we refer to α as the heat diffusion coefficient, which is generally spatially dependent.

In general, for heat conduction in non-homogeneous anisotropic media, the study of heat conduction is based on several principles. Heat flow is a form of energy flow, and as such it is meaningful to speak of the time rate of flow of heat into a region of space. The time rate of heat flow into a region V is given by a time-dependent quantity $q_t(V)$. We assume that q has a density, so that $$q_t(V) = \int_V Q(x,t)dx. \quad (4)$$

The heat flow is a time-dependent vector function H(x) characterized as follows. The time rate of heat flowing through an infinitesimal surface element with area d S and with unit normal vector n is $$H(x) \cdot n(x) dS. \quad (5)$$

Thus, the rate of heat flow into V is also given by the surface integral $$q_t(V) = -\int_{\partial V} H(x) \cdot n(x) dS, \quad (6)$$

where n(x) is the outward pointing normal vector at x.

The Fourier law states that heat energy flow has the following linear dependence on the temperature gradient $$H(x) = -A(x) \cdot \nabla u(x), \quad (7)$$

where A(x) is a 3×3 real matrix that is symmetric and positive definite. By Green's theorem, the previous surface integral for heat flow into V can be transformed into the volume integral $$q_t(V) = -\int_{\partial V} H(x) \cdot n(x) dS \quad (8)$$

$$= \int_{\partial V} A(x) \cdot \nabla u(x) \cdot n(x) dS$$

$$= \int_V \sum_{i,j} \partial_{x_i} \left( a_{ij}(x) \partial_{x_j} u(x,t) \right) dx.$$

The time rate of temperature change at x is proportional to the heat flowing into an infinitesimal volume element, where the constant of proportionality is dependent on a constant κ

$$\partial_t u(x,t) = \kappa(x) Q(x,t). \quad (9)$$

Putting the above mentioned equations together gives the general equation of heat flow:

$$\partial_t u(x,t) = \kappa(x) \sum_{i,j} \partial_{x_i} \left( a_{ij}(x) \partial_{x_j} u(x,t) \right). \quad (10)$$

It should be noted that the coefficient κ(x) is the inverse of specific heat of the substance at x×density of the substance at x, and that, in the case of an isotropic medium, the matrix A is a scalar matrix equal to thermal conductivity. In the anisotropic case where the coefficient matrix A is not scalar (i.e., if it depends on x), an explicit formula for the solution of the heat equation can seldom be written down. Though, it is usually possible to consider the associated abstract Cauchy problem and show that it is a well-posed problem and/or to show some qualitative properties (like preservation of positive initial data, infinite speed of propagation, convergence toward an equilibrium, smoothing properties). This is usually done by one-parameter semigroups theory. For instance, if A is a symmetric matrix, then the elliptic operator defined by $$Au(x) := \sum_{i,j} \partial_{x_i} a_{ij}(x) \partial_{x_j} u(x) \quad (11)$$

is self-adjoint and dissipative, thus by the spectral theorem it generates a one-parameter semigroup.

Using the above mentioned mathematical framework, the second temperature distribution evolution in space and over time can be estimated. For the initialization of the calculation, the temperature can be set to the measured temperature distribution at time t=0, and the temperature at the position of the energy-supplying electrodes can be defined as the function of temperature over time at these locations given by the electrode vendor for a specific setting of the power supply parameters.

As mentioned, the function of temperature over time at the location of the electrodes is determined by the parameters of the power supply feeding the electrodes (or in the general case by the spatially dependent energy supplied by the energy-providing device). The vendor of the electrodes provides planning software, which predicts how the temperature distribution will evolve in space over time. Obviously, this prediction is based on certain quite general assumptions about the heat conductivity of the tissue surrounding the electrodes: the iso-temperature contours are typically spherical, and their propagation over time depends on the function of the electrode supply current over time.

In practice, a different temperature distribution will evolve, as measured in the first temperature range in the above-described fashion, exhibiting significant deviations from spherical shape and uniform propagation over time. Since, however, the thus observed temperature distribution is based on the same current supply function over time, the actually evolving distribution can be predicted with better quality if the local heat diffusion coefficients (local heat conductivity) are known or can be estimated, and fed into the heat diffusion mathematical framework.

Still, in general, there will be deviations between the observed iso-contours and the local propagation speed, also from the improved predictions. These deviations can be fed into an iterative algorithm which will allow to derive improved information about the local heat diffusion coefficients (local heat conductivity) and vessel cooling effects, which can then be used for the extrapolating the temperature distribution into the second temperature range.

Based on the initially available and/or iteratively refined knowledge of the local heat diffusion coefficients (local head conductivity), the second temperature distribution can be calculated—based on the above mathematical framework—for any function of electrode current over time. This ability allows to recommend modifications of the electrode current parameter settings to the user, in order to have the estimated temperature distribution in the therapeutic, ablative temperature range optimally match the planned/targeted ablation region.

Figure 4:
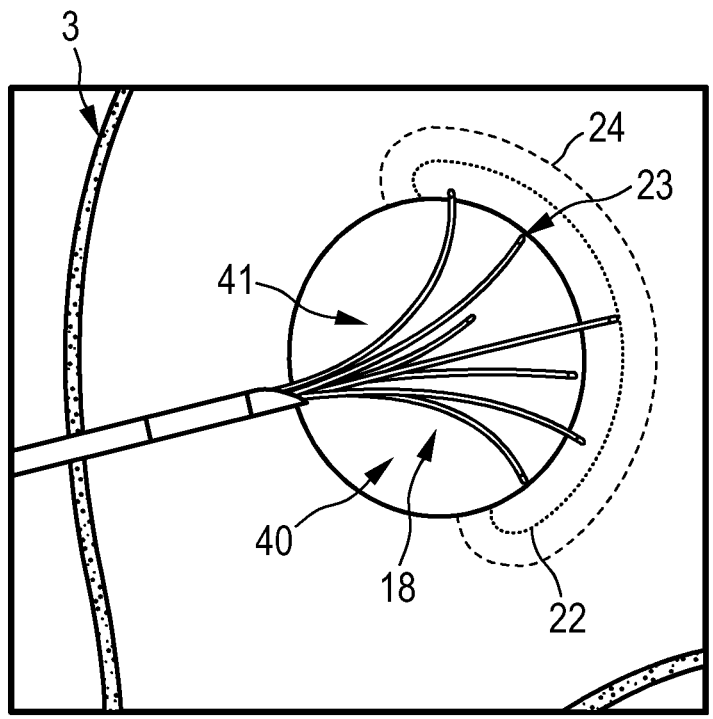

FIG. 4 shows schematically and exemplarily an estimated influence region 24 which has been determined by the estimated influence region determining unit 8 depending on the estimated second temperature distribution, wherein the estimated influence region is indicative of the region of the object, in which the object is influenced to a predefined degree by the application of energy. In this embodiment, the predefined degree of the influence by the application of energy is reached, if the respective region of the object comprises cells for which death has been induced by coagulation. In other embodiments, another degree of influence by the application of energy can be predefined.

The temperature distribution determining apparatus 1 further comprises an influenced deviation determining unit 9 for determining a deviation between the estimated influence region 24 and the predefined influence region 22, and an energy application characteristics adaptation unit 10 for adapting the provided energy application characteristics depending on the determined deviation. Since the energy application characteristics adaption unit 10 is configured for adapting the provided energy application characteristics depending on the determined deviation between the estimated influence region 24 and the predefined influence region 22, the application of energy can be corrected such that the finally influenced region will better match the predefined influence region 22. Preferentially, the energy application characteristics adaption unit 10 adapts the provided energy application characteristics depending on the determined deviation, wherein the second temperature distribution and the estimated influence region are calculated again on the basis of the adapted energy application characteristics, until the deviation between the actually estimated influence region and the predefined influence region is below a predefined threshold or until a predefined number of iterations has been performed.

The actual estimated ablation zone, i.e. the actually estimated influence region, as predicted based on the extrapolation of the three-dimensional temporal and spatial first temperature distribution into the therapeutic temperature range of about 60° C., is compared with the originally planned target zone, i.e. the predefined influence region, and the energy application characteristics adaption unit 10 computes, for example, improved power level settings which can be applied in the below described phase three. For example, the power settings can be adjusted such that the predefined influence region is included within the estimated influence region with a safety margin. If the position of the ablation electrodes with respect to the object should be adapted, the temporally and spatially depending first temperature distribution is preferentially measured again with the new positions of the ablation electrodes. The positions of the ablation electrodes can be determined by known methods. For example, a computed tomography image can be reconstructed in which the ablation electrodes are visible for determining the locations of the ablation electrodes. Or, an X-ray fluoroscopy system can be used for determining the locations of the ablation electrodes.

Alternatively or in addition to adapting the provided energy application characteristics by the energy application characteristics adaption unit 10 depending on the determined deviation, the energy application characteristics providing unit 4 can be adapted to allow a user to modify the provided energy application characteristics, based on recommendations derived by utilizing the above-mentioned mathematical framework approach, wherein the temperature distribution estimating unit 5 is adapted for estimating a modified second temperature distribution in the object within the second temperature range, which would be present, if the energy would be applied to the object in accordance with the modified provided energy application characteristics, based on the measured first temperature distribution and the modified provided energy application characteristics, wherein the estimated influence region determining unit 8 is adapted for determining a modified estimated influence region of the object 3 depending on the estimated modified second temperature distribution. For example, the input device 11 can be used for allowing a user to modify the provided energy application characteristics, in particular, the automatically adapted provided energy application characteristics.

The temperature distribution determining apparatus 1 further comprises a display 12 for showing an overlay image of the estimated influence region 24 and the predefined influence region 22. The user can modify the energy application characteristics and the estimated influence region of the object can be updated depending on the modified energy application characteristics. This allows a user to modify, for example, the power settings, until a desired estimated influence region has been obtained. Moreover, it allows a user to correct the automatically adapted provided energy application characteristics and to monitor the effect of the user's correction on the estimated influence region.

In a third phase, which can be regarded as an adjusted ablation therapy execution phase, the provided energy application characteristics, which may be adapted by the energy application characteristics adaption unit 10 and/or modified by the user, are applied to the object and the ablation procedure is performed. It should be noted that before the third phase preferentially energy has been applied to the object 3 only while measuring the first temperature distribution in the first temperature range, i.e. before the third phase the object has not been heated to a therapeutic temperature, at which, for example, cell death is induced by coagulation.

In the third phase the temperature distribution measuring unit 6, 7 can measure a third temperature distribution in the object 3 in the first temperature range in a first part of the object 3, while the energy is applied to the object in accordance with the provided energy application characteristics, which may have been adapted or modified, if the first part of the object 3 has a temperature within the first temperature range and a second part of the object 3 has a temperature within the second temperature range. The temperature distribution estimating unit 5 is adapted for estimating a fourth temperature distribution in the second part of the object 3 within the second temperature range, which is present while the energy is applied to the object 3 in accordance with the provided applied energy application characteristics, based on at least one of the measured first temperature distribution, the estimated second temperature distribution and the measured third temperature distribution. The estimated influence region determining unit 8 can be adapted to determine the estimated influence region of the object 3 depending on the estimated fourth temperature distribution. The influenced deviation determining unit 9 is then preferentially adapted to determine a deviation between the estimated influence region, which has been estimated depending on the fourth temperature distribution, and the predefined influence region, wherein the energy application characteristics adaption unit 10 can be configured to adapt the energy application characteristics, which describes the current application of energy to the object, depending on the determined deviation. Thus, even during the application of energy in the third phase the temperature distribution can be determined and the application of energy can be adapted in accordance with the determined temperature distribution. In addition or alternatively, the actual estimated influence region, which is determined based on the fourth temperature distribution preferentially continuously, can be shown on the display 12, in particular, by showing an overlay image of the actual estimated influence region and the predefined influence region, and the user can modify the energy application characteristics by using the input unit 11, if the estimated influence region does not develop as desired. The user can also stop the energy application procedure by using the input unit 11. Thus, also in the third phase, the ultrasound thermometry can be applied, in order to see how the three-dimensional temperature distribution evolves. Since the periphery of the ablation zone will still have temperatures below 55° C., the temperature measurement will still work in this area and allow for a comparison between the newly measured third temperature distribution and the updated predictions generated in the second phase and/or a comparison between the shape of the measured iso-contours, as they evolve in the first temperature range, with the shape of the initially predefined influence region.

A correspondence measure can be calculated based on a number of criteria. Preferentially, the correspondence measure is calculated based on the agreement between a predicted ablation region, i.e. an estimated influence region, and a targeted ablation region, i.e. the predefined influence region, which is, in this embodiment, based on the tumor shape and size. The achieved ablation zone should be larger than the tumor, with some predefined margin, in order to optimally prevent tumor recurrence. The only instance in which incomplete coverage of the tumor is accepted occurs when important healthy tissue structures will be ablated in case the tumor is fully covered. This can be the case, if in the liver, a vessel feeding a large, healthy liver lobe is at risk and likely to be ablated. Therefore, the correspondence measure can be implemented as the ratio r of the tumor volume $t_a$, i.e. the targeted ablation region, covered by the predicted ablation zone over the total tumor volume $t_t$, $r = t_a/t_t$, multiplied by a risk factor f, which can be calculated e.g. as $f = (1 - h/t_t)$, with h being the volume of healthy tissue likely to be ablated. This leads to a correspondence measure $c = r*f = t_a/t_t*(1-h/t_t)$.

The temperature distribution estimating unit 5 can, as explained above, be adapted for estimating a fourth temperature distribution in the second part of the object 3 within the second temperature range. In addition or alternatively, the temperature distribution determining apparatus 1 can comprise a degree of correspondence determining unit 25 for determining a degree of correspondence between the estimated second temperature distribution in the second part of the object and the measured third temperature distribution in the first part of the object, while the provided energy is applied to the object. If the degree of correspondence is below a predefined threshold, this can be shown on the display 12 for indicating that the calculation for estimating the second temperature distribution and, thus, the determination of the estimated influence region may not be correct. For example, if energy is applied to the object such that the second part of the object, in which the object has been heated to the second temperature range, is located around the electrodes and the first part of the object, in which the object has not been heated up to the second temperature range, i.e. in which the object is in the first temperature range, is more far away from the electrodes, the measured third temperature distribution may define the first part and the part of the object, in which the third temperature distribution cannot be measured, can define the second part of the object. Thus, indirectly the third temperature distribution can define the second part of the object. Moreover, the second part of the object can also be defined by the estimated second temperature distribution. A degree of correspondence between the estimated second temperature distribution and the measured third temperature distribution can then be defined depending on, for example, the volume of the second part of the object defined by the estimated second temperature distribution and the volume of the second part of the object defined by the measured third temperature distribution. For example, a difference or a ratio of these two volumes can be used as a degree of correspondence.

If the predicted ablation region deviates too strongly from the desired target zone, indicated for example by the above mentioned degree of correspondence between the estimated second temperature distribution in the second part of the object and the measured third temperature distribution in the first part of the object and/or indicated by the also above mentioned correspondence measure between the predicted ablation region and the targeted ablation region, the user can stop the application of applying energy to the object and/or the temperature distribution determining apparatus can be adapted to automatically stop the application of energy to the object. Then, for example, the second temperature distribution and the estimated influence region can be determined again for obtaining an improved second temperature distribution and, thus, an improved estimated influence region. This can also be used to initiate the use of more complex algorithms incorporating more knowledge about heat diffusion coefficients and the cooling effect of blood flowing through the vessels, i.e. algorithms which may be more time consuming and would thus only be used in complicated cases.

The temperature distribution determining apparatus can also be adapted to compare the third temperature distribution, after the application of energy has been started in the third phase, with the first temperature distribution measured in the first phase. For example, a further correspondence measure can be calculated as the inverse of: The absolute difference between the two iso-contours for, for instance, 50° C. of the first temperature distribution and the third temperature distribution, divided by the sum of these two volumes. Thus, if $v_1$ is the volume inside the 50° C. iso-contour of the first temperature distribution and if $v_3$ is the volume inside the 50° C. iso-contour of the third temperature distribution, the correspondence measure may be defined by $(v_1+v_3)/abs(v_1-v_3)$. Also this correspondence measure can be used to automatically abort the application of energy or to automatically modify the energy application characteristics, if the correspondence measure exceeds a predefined threshold. In addition or alternatively, also this correspondence measure can be shown on a display, and a user can modify or abort the application of energy depending on the displayed correspondence measure. If the energy application characteristics are modified, the first temperature distribution is preferentially measured again, and, after the application of energy has been started again in the third phase with the modified energy application characteristics, the correspondence measure can be calculated again based on the first temperature distribution newly measured in the first phase in accordance with the modified energy application characteristics and the third temperature distribution newly measured in the third phase also in accordance with the modified energy application characteristics.

The temperature distribution determining apparatus 1 further comprises an influenced region determining unit 14 for determining an influenced region being indicative of the region of the object 3, in which the object has been influenced to a predefined degree by the application of energy. In this embodiment, a part of the object has been influenced to a predefined degree, if this part is coagulated such that cell death has been induced. The influenced region determining unit 14 is preferentially adapted to determine an elasticity distribution within the object from the ultrasound data acquired by the ultrasound unit 6 by using ultrasound elastography. In this embodiment, if in a region the elasticity indicates a stiffness being larger than a stiffness threshold, this region is regarded as belonging to or representing the influenced region, because it is known that the coagulation zone is stiffer than vital tissue. The stiffness threshold can be determined by calibration measurements, wherein during the calibration measurements it is known which part of the object has been coagulated and which part of the object has not been coagulated. Alternatively, a computed tomography or magnetic resonance imaging or magnetic resonance elastography scan can be taken in order to assess the coagulation zone in three dimensions. Thus, in a fourth phase the ablation volume can be verified and patient outcome can be predicted based on the achieved result. Based on a comparison with initial diagnostic image data, the clinician can create a statement as to how well the target volume has been ablated and with what kind of safety margin.

The temperature distribution calculation unit 7, the temperature distribution estimating unit 5, the energy application characteristics providing unit 4, the estimated influence region determining unit 8, the influenced deviation determining unit 9, the energy application characteristics adaptation unit 10, the object structure providing unit 13, the influenced region determining unit 14 and the degree of correspondence determining unit 25 are integrated in a calculation unit 15. In other embodiments, one or several of these units may not be integrated into a single calculation unit.

The temperature distribution determining apparatus 1 comprises a catheter control unit 19 including the RF energy source 20 and a guiding control unit 21 for guiding the catheter tip 18 to a desired location within the object 3. The guiding control unit 21 controls, in this embodiment, built-in guiding means (not shown in FIG. 1) of the catheter 2. The catheter 2 can be steered and navigated by the use of steering wires or other mechanical means in order to guide the catheter tip 18 to the desired location within the object 3. The steering wires or other mechanical means for steering and navigating the catheter tip can be controlled by the guiding control unit 21.

The above described energy application unit comprises the RF energy source 20 and the ablation electrodes 23, wherein the ablation electrodes are located at the catheter tip 18 and are connected with the RF energy source via electrical connections like wires. The energy application unit preferentially further comprises a grounding electrode as it is known in state-of-the-art RF ablation systems. In another embodiment, alternatively or in addition to comprising a catheter with a catheter tip, the temperature distribution determining apparatus can comprise a needle with a needle tip comprising an electrode for applying energy to the object. The temperature distribution determining apparatus comprises then further a needle control unit including an RF energy source and a guiding control unit for guiding the needle tip to a desired location within the object. Also in this embodiment, the guiding control unit controls built-in guiding means of the needle. For example, the needle can be steered and navigated by the use of steering wires or other mechanical means like a robotic needle insertion device. The needle tip comprises preferentially one or several ablation electrodes which are connected with the RF energy source via electrical connections like wires.

Although the above described ultrasound unit generates two-dimensional ultrasound data, also a three-dimensional ultrasound unit can be used for generating three-dimensional ultrasound data, wherein the ultrasound data form a three-dimensional ultrasound image which can be shown on the display 12. The temperature distribution calculation unit is then adapted to calculate the first temperature distribution based on the three-dimensional ultrasound data.

Figure 5:
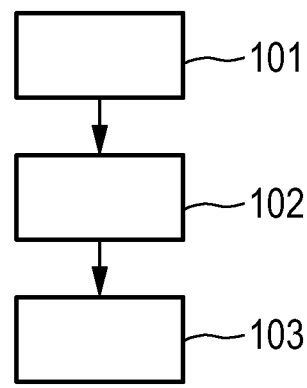
FIG. 5 shows a flowchart exemplarily illustrating an embodiment of a temperature distribution determining method for determining a temperature distribution within an object caused by applying energy to the object.

In the following an embodiment of a temperature distribution determining method will exemplarily be described with reference to a flowchart shown in FIG. 5.

In step 101, a first temperature distribution is measured in the object 3, while energy is applied to the object 3 such that the object 3 is heated to a temperature within a first temperature range, by the temperature distribution measuring unit. In particular, ultrasound data are acquired by the ultrasound unit 6 and the temperature distribution calculation unit 7 calculates the first temperature distribution depending on the acquired ultrasound data. The object 3 is heated from about 37° C. to a temperature such that the resulting first temperature region provides sufficient information for estimating a second temperature distribution within a second temperature range being different to the first temperature range. For example, the first temperature range can be from about 37° C. to about 50° C., and the second temperature range can be arranged around 60° C.

In step 102, energy application characteristics describing the application of energy to the object such that the object is heated to a temperature within a second temperature range are provided by the energy application characteristics providing unit 4. For example, power level settings and the locations of the ablation electrodes with respect to the object can be provided. In step 103, the second temperature distribution in the object within the second temperature range is estimated, wherein the second temperature distribution would be present, if the energy would be applied to the object in accordance with the provided energy application characteristics. The estimation is performed based on the measured first temperature distribution by the temperature distribution estimating unit 5.

The temperature distribution determining apparatus can be used for performing a thermal therapy as a non- or minimally invasive approach for the treatment of tumors alternative to surgical resection. For applying the energy to the object, in particular, for performing the thermal treatment, energy can be applied to the object by various techniques like RF ablation, lasers, therapeutic ultrasound, microwaves, et cetera. During the thermal therapy tissue is heated locally preferentially up to above 60° C., and cancerous tissue is thereby destroyed by coagulation. The temperature distribution determining apparatus can be used, for example, in the field of liver cancer or in the field of another kind of cancer.

If cancer should be treated, known ablation techniques often leave seed cells behind in the object because of, for example, inadequate planning and/or inadequate ablation. In the prior art, inadequate planning occurs very frequently because the cooling effect from blood vessels is very difficult to predict, and most planning tools are based on the assumption of spherical iso-contours around the electrode tips. The temperature distribution determining apparatus is preferentially adapted to eliminate or minimize this drawback by providing a better planning, monitoring and adjustment of the thermal "dose" during the ablation process. The ablation electrodes 23 and the RF energy source 20 are preferentially adapted such that at least some, preferably all, of the ablation electrodes 23 can be controlled separately regarding their heat deposition. As can be seen in FIGS. 3 and 4 the advanced ablation electrodes are located at several sub tips 41 extending from the catheter tip 18. If, in another embodiment, a needle with a needle tip is used, also this needle tip can comprise several sub tips, which can be advanced from the needle and which can comprise ablation electrodes. Preferentially, each of the sub tips 41 has a thermocouple incorporated, which allows continuous monitoring of tissue temperatures, and each sub tip power is automatically adjusted so that the target temperatures remain constant. The catheter control unit 19 comprises therefore further a temperature monitoring unit 26 being connected to the thermocouples for monitoring the temperature at the sub tips 41. The tip power values, and preferentially the temporal pattern in which they are applied, can be adjusted in a manner which allows for some degree of shaping of the resulting ablation volume, which is, in the prior art, normally assumed to be spherical, i.e. normally the inhomogeneity of the tissue, which leads to strong deviations from this spherical shape, is neglected.

A prerequisite for the adaptation of power levels is an indication of the actually ablated tissue area, which is optimally be achieved through real-time monitoring of the in-vivo three-dimensional temperature distribution in the body. In the prior art, this can only be achieved with reasonable accuracy through magnetic resonance imaging, but using a magnetic resonance scanner as a three-dimensional thermometer only is very expensive. Therefore, it has been proposed to use computed tomography for the purpose of temperature measurement, but this temperature measurement is very inaccurate, for example, the temperature measurement is only possible with an accuracy of about 5° C. An ultrasound unit acquires ultrasound data, which can be used for placing the ablation electrodes into the object, in particular, into the tumor, through ultrasound-image guidance. But, in the prior art the ultrasound data cannot be used for three-dimensional thermometry in the therapeutic ablation temperature range comprising temperatures of, for example, 60° C. or higher. The temperature distribution determining apparatus is preferentially adapted to overcome this limitation by estimating a second temperature distribution within a second temperature range being preferentially the therapeutical ablation temperature range.

The temperature distribution determining apparatus improves preferentially monitoring, re-planning and outcome prediction for RF ablation, especially of liver tumors, in order to reduce present high recurrence rates which are largely caused by deviations between the planned versus the achieved ablation zone. In the prior art, generally the ablation zone is assumed to have a spherical shape for a single electrode position, while in reality the shape of the actually ablated region deviates substantially from this assumption. For example, indentations around the ablation electrodes and major indentations caused by cooling effects from blood vessels can be present. The estimation of the ablation zone during the therapy procedure allows a clinician to adjust the electrode tip power levels, in order to compensate for undesired deviations of the evolving ablation volume from the initially planned shape and extent, and, thus, substantially reduce the probability of tumor recurrence due to undertreated areas of the tumor as well as a probability of unwanted damage of healthy tissue. The temperature distribution determining apparatus is therefore preferentially adapted to use the information about the evolution of the three-dimensional temperature distribution in the first temperature range, preferentially measured by using ultrasound thermometry, for adjusting the power levels for the ablation electrodes in a suitable manner as to achieve a better agreement of the achieved ablation volume, i.e. the influenced region, with the target volume, i.e. the predefined influence region. The target volume for the ablation can be available from an initial planning performed by clinical experts. In an embodiment, the target volume can be defined by one or more electrode locations relative to the object, and a spherical ablation zone around each of these locations.

A single unit or device may fulfill the functions of several items recited in the claims. The mere fact that certain measures are recited in mutually different dependent claims does not indicate that a combination of these measures cannot be used to advantage.

Figure 6:
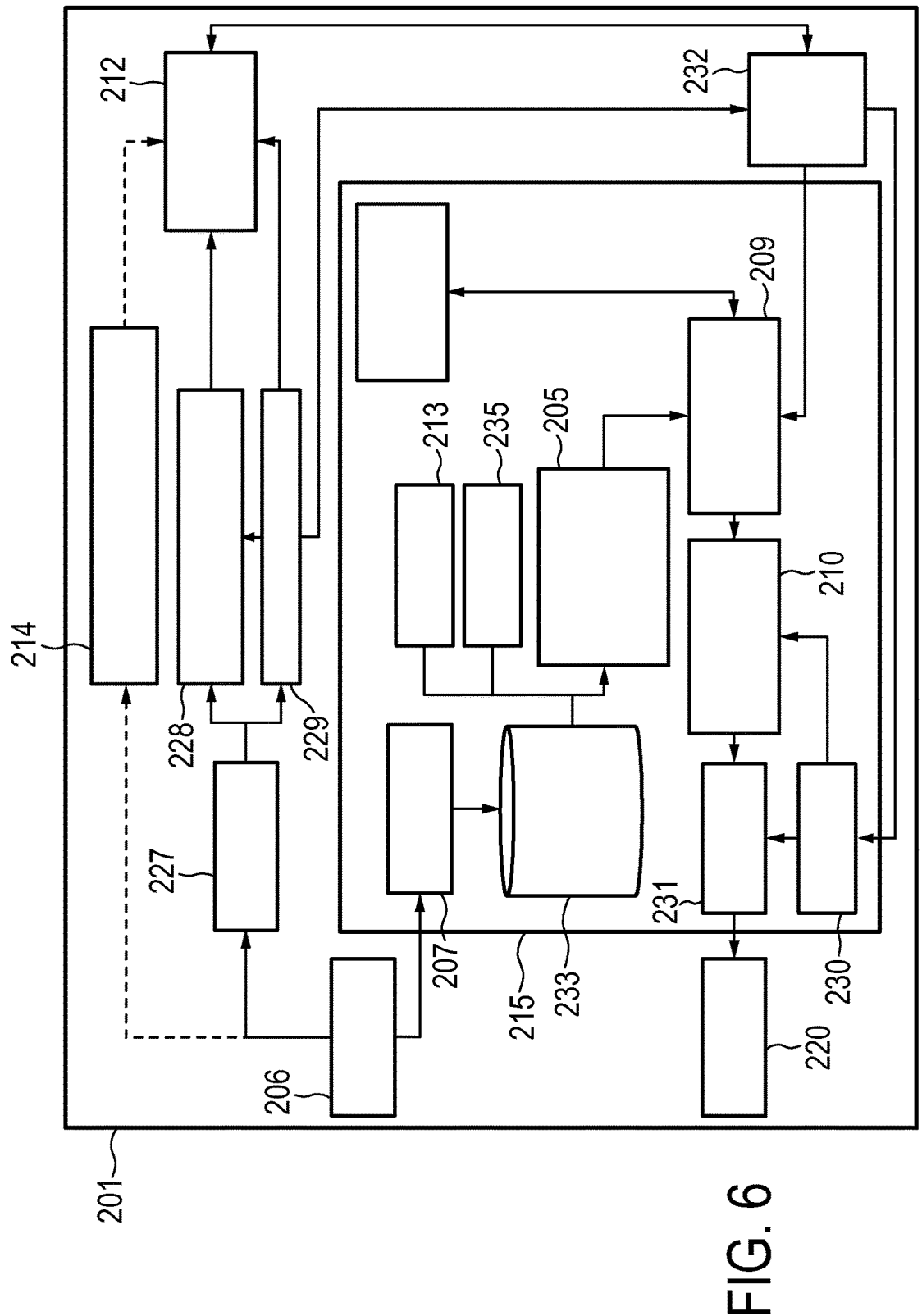
FIG. 6 shows schematically and exemplarily a further embodiment of a temperature distribution determining apparatus for determining a temperature distribution within an object caused by applying energy to the object.

Calculations, determinations, estimations, et cetera, like the calculation of the first temperature distribution or the estimation of the second temperature distribution, performed by one or several units or devices can be performed by any other number of units or devices. For example, the calculations, estimations and determinations described above as being performed by several units, can also be performed by a single unit or by any other number of different units. The calculations, determinations, estimations, et cetera, and/or the control of the temperature distribution determining apparatus in accordance with the temperature distribution determining method can be implemented as program code means of a computer program and/or as dedicated hardware. An embodiment of such a computer program, which can also be implemented as dedicated hardware, will in the following be described with reference to FIG. 6.

The computer program is incorporated into an image-guided therapy system 201 being an embodiment of a temperature distribution determining apparatus. The image-guided therapy system 201 comprises a therapy monitoring and control workstation 215. A three-dimensional ultrasound transducer 206 for generating three-dimensional ultrasound data provides these data to a three-dimensional ultrasound imaging unit 227 for generating a three-dimensional ultrasound image based on the provided three-dimensional ultrasound data. The three-dimensional ultrasound images are then preferentially used by an image-guided RFA electrode placement module 228 for placing an RFA (radiofrequency ablation) electrode, which can also be regarded as an RFA needle, based on the provided three-dimensional ultrasound image. For this placement procedure also an initial lesion is used, which has been assessed by an initial lesion assessment unit 229. The initial lesion is preferentially assessed based on the three-dimensional ultrasound image. The three-dimensional ultrasound image, the placed RFA electrode, the initial lesion, et cetera can be displayed on a display 212 which is preferentially used for viewing images and for user communication purposes. Thus, the image-guided therapy system 201 can be used for the initial ultrasound imaging, for lesion assessment, for planning of a standard ablation, wherein one or several surgical target zones are defined, and for image-guidance for interactive electrode placement into the lesion. The image-guided therapy system 201 further comprises an ablation target zone definition unit 232 for defining an ablation target zone, i.e. for defining an influence region, based on the initial lesion assessment.

Based on the predefined ablation target zone a vendors' RFA planning unit 230 of the therapy monitoring and control workstation 215 determines the power level settings of the ablation electrodes such that the predefined ablation target zone is covered. The vendors' RFA planning unit 230 uses vendors' information regarding the radius of an ablation sphere around the respective ablation electrode depending on the applied power. The power level settings can be provided to an RFA power control unit 231 for controlling an RFA electrode power supply 220, which is electrically connected to the ablation electrodes for applying energy to the object. The image-guided therapy system 201 can therefore initiate a standard RF ablation.

The therapy monitoring and control workstation 215 further comprises a three-dimensional ultrasound thermometry unit 207 for calculating a temporally dependent three-dimensional spatial first temperature distribution within the first temperature range. The three-dimensional first temperature distribution, which has been measured over time, is then stored in a storing unit 233. Thus, in a first phase being a monitoring phase ultrasound thermometry is performed and the resulting three-dimensional first temperature distribution, which has been measured over time, is stored.

The therapy monitoring and control workstation 215 further comprises a temperature distribution estimating unit 205 for estimating a second temperature distribution in a second temperature range being, in this embodiment, a therapeutic ablation temperature range in which cells coagulate for inducing cell death. The temperature distribution estimating unit 205 is preferentially adapted to extrapolate a three-dimensional second temperature distribution within the therapeutic ablation temperature range by using the measured and stored first temperature distribution, heat diffusion equations provided by a heat diffusion equation providing unit 235 and three-dimensional tissue characteristics, potentially including vessel location and local flow velocity information, provided by an object structure providing unit 213. An influenced deviation determining unit 209 determines a deviation between an estimated influence region, which is estimated depending on the provided second temperature distribution, and the target ablation volume. The deviation result is then provided to an energy application characteristics adaptation unit 210 for adapting the energy application characteristics depending on the deviation provided by the influenced deviation determining unit 209. In this embodiment, the energy application characteristics adaption unit 210 computes adjusted electrode power settings based on the provided deviation and the electrode power settings provided by the vendors' RFA planning unit 230. Thus, in a re-planning and plan adjustment phase, i.e. the second phase, preferentially the three-dimensional first temperature distribution is extrapolated to the second, therapeutic ablation temperature range for estimating the second temperature distribution, wherein the heat diffusion equations and potentially available knowledge about tissue characteristics, such as locally varying heat diffusion coefficients, blood vessel locations and local flow velocity in these vessels, are taken into account. The resulting predicted ablation volume, i.e. the estimated influence region, is then compared to the initially defined ablation target zone, i.e. the predefined influence region. New electrode power settings are then generated by the energy application characteristics adaptation unit 210. In the third phase, the generated, i.e. adjusted, electrode power settings are then—based on a suitable interaction with the clinical expect and his or her confirmation/approval—loaded into the RFA power control unit 231, which may be provided by the RFA vendor, for the actual therapy delivery of the proposed procedure.

The image-guided therapy system 201 optionally further comprises an ultrasound elastography unit 214 for determining the actually ablated volume, i.e. the influenced region, to be used as the basis for recurrence/outcome prediction.

In particular, at least one, preferentially all, of the three-dimensional ultrasound thermometry unit 207, the influenced deviation determining unit 209, the energy application characteristics adaptation unit 210, the temperature distribution estimating unit 205, the ultrasound elastography unit 214, the heat diffusion equation providing unit 235, the three-dimensional ultrasound imaging unit 227, the initial lesion assessment unit 229, the vendors' RFA planning unit 230 and the RFA power control unit 231 can be provided as program code means of a computer program, which is incorporated into the image-guided therapy system 201.

The different units described above with reference to FIG. 6, which perform calculations, determinations and estimations, are provided as program code means of a computer program, which is incorporated into the image-guided therapy system 201.

In a further embodiment, the temperature distribution measuring unit for measuring a first temperature distribution in the object, while the energy is applied to the object such that the object is heated to a temperature within a first temperature range, can be adapted for measuring several first temperature distributions in the object, while the energy is applied to the object in accordance with several measurement energy application characteristics such that the object is heated to different temperatures within the first temperature range. Moreover, the temperature distribution estimating unit for estimating the second temperature distribution can be adapted such that the second temperature distribution is estimated based on the several measured first temperature distributions measured at the several measurement energy application characteristics and the provided energy application characteristics. Also in this embodiment, the temperature distribution estimating unit estimates the second temperature distribution based on extrapolation, wherein the several measured first temperature distributions measured at the several measurement energy application characteristics are extrapolated to the provided energy application characteristics.

Although in the above described embodiments RF energy is applied to the object, also other kinds of energy can be applied to the object like another kind of electrical energy such as microwaves, optical energy, ultrasound energy, nuclear energy, et cetera. The temperature distribution determining apparatus is preferentially adapted to be applied for thermal therapy approaches which are compatible with intra-therapy ultrasound imaging. Although in the above described embodiments a certain kind of ablation electrode has been described for applying RF energy, also one or several ablation electrodes having another structure can be used for applying RF energy.

Although the above described embodiments of the temperature distribution determining apparatus comprise an energy application unit, the temperature distribution determining apparatus can also be a separate apparatus which does not comprise the energy application unit. This separate temperature distribution determining apparatus is then adapted to cooperate with an energy application apparatus for applying energy to an object.

Although in the above described embodiments the temperature has been determined within an organ of a person, the temperature distribution determining apparatus can also be adapted to determine the temperature within another part of a person or within another object like an animal, a plant, or a technical object.

Although in the above described embodiments certain first and second temperature ranges have been defined, the temperature distribution determining apparatus and method can also be adapted to measure and estimate first and second temperature distributions, respectively, in other temperature ranges. In particular, the first temperature range preferentially depends on the temperature range within which the respective used temperature distribution measuring unit can measure the first temperature distribution, and the second temperature range is preferentially a therapeutic temperature range in which a desired therapeutic effect can be obtained. For example, if energy should be applied to tissue for direct tumor cell killing, the second temperature range may be 45° C. to 70° C., preferentially 50° C. to 70° C. and further preferred 55° C. to 65° C. Or, if, for example, cells should be made more susceptible to concomitant radio- or chemotherapy, the second temperature range may be 40° C. to 50° C., preferentially 41° C. to 46° C., and further preferred 44° C. to 46° C. The first temperature range and the second temperature range can be overlapping temperature ranges, or they can be non-overlapping temperature ranges, in particular, the first temperature range and the second temperature range can be adjacent to one another.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a temperature distribution determining apparatus for determining a temperature distribution within an object caused by applying energy to the object. A temperature distribution measuring unit measures a spatially and temporally dependent first temperature distribution in the object, while the energy is applied to the object such that the object is heated to a temperature within a first temperature range, and a temperature distribution estimating unit estimates a spatially and temporally dependent second temperature distribution in the object within a second temperature range, which is different to the first temperature range, based on the spatial and temporal dependence of the measured first temperature distribution. Since temperature distributions can be obtained not only in the first temperature range, but also in the second temperature range, the overall temperature range, in which the temperature distribution can be determined, can be increased.

The invention claimed is:

1. A temperature distribution determining apparatus for determining a temperature distribution within an object caused by applying energy to the object, the temperature distribution determining apparatus (1) comprising:
    a temperature distribution measuring unit (6, 7) for measuring a spatially and temporally dependent volumetric first temperature distribution in the object (3), while the energy is applied to the object (3) such that the object (3) is heated to a temperature within a first temperature range,
    a temperature distribution estimating unit (5) for estimating a spatially and temporally dependent second temperature distribution in the object (3) within a second temperature range, which is different to the first temperature range and in which the temperature distribution measuring unit (6, 7) cannot measure a temperature distribution, based on a spatial and temporal extrapolation of the measured volumetric first temperature distribution,
    wherein the temperature distribution determining apparatus (1) further comprises an estimated influence region determining unit (8) for determining an estimated influence region of the object (3) depending on the estimated second temperature distribution, wherein the estimated influence region is indicative of the region of the object (3), in which the object (3) is influenced to a predefined degree by the application of energy and comprising a display (12) for showing an overlay image of the estimated influence region and a predefined influence region.

2. The temperature distribution determining apparatus as defined in claim 1, wherein the temperature distribution measuring unit (6, 7) comprises an ultrasound unit (6) for acquiring ultrasound data from the object (3) and a temperature distribution calculation unit (7) for calculating the volumetric first temperature distribution depending on the acquired ultrasound data.

3. The temperature distribution determining apparatus as defined in claim 1, wherein the temperature distribution estimating unit (5) is adapted to extrapolate the measured volumetric first temperature distribution from the first temperature range into the second temperature range for estimating the second temperature distribution.

4. The temperature distribution determining apparatus as defined in claim 1, wherein it is assumed that the energy is applied to the object such that a temperature of the object is changed from a temperature within the first temperature range to a temperature within the second temperature range, wherein the temperature distribution estimating unit (5) is adapted to extrapolate the measured volumetric first temperature distribution from time points, at which the object has a temperature within the first temperature range, to time points, at which the object has a temperature within the second temperature range.

5. The temperature distribution determining apparatus as defined in claim 1, wherein the temperature distribution determining apparatus further comprises:
   an energy application characteristics providing unit (4) for providing energy application characteristics describing the application of energy to the object (3) such that the object (3) is heated to a temperature within the first temperature range, while the temperature distribution measuring unit (6, 7) measures the volumetric first temperature distribution, and further to a temperature within the second temperature range,
   an influenced deviation determining unit (9) for determining a deviation between the estimated influence region and a predefined influence region,
   an energy application characteristics adaption unit (10) for adapting the provided energy application characteristics depending on the determined deviation.

6. The temperature distribution determining apparatus as defined in claim 1, wherein the temperature distribution determining apparatus comprises an energy application characteristics providing unit (4) for providing energy application characteristics describing the application of energy to the object (3) such that the object (3) is heated to a temperature within the second temperature range, wherein the energy application characteristics providing unit (4) is adapted for allowing a user to modify the provided energy application characteristics, wherein the temperature distribution estimating unit (5) is adapted for estimating a modified second temperature distribution in the object within the second temperature range, which would be present, if the energy would be applied to the object (3) in accordance with the modified provided energy application characteristics, wherein the estimated influence region determining unit (8) is adapted for determining a modified estimated influence region of the object (3) depending on the estimated modified second temperature distribution.

7. The temperature distribution determining apparatus as defined in claim 1, wherein the temperature distribution determining apparatus comprises an energy application characteristics providing unit (4) for providing energy application characteristics describing the application of energy to the object (3) such that the object (3) is heated to a temperature within the second temperature range, wherein the temperature distribution measuring unit (6, 7) is adapted for measuring a third temperature distribution in the object (3) in the first temperature range in a first part of the object (3), while the energy is applied to the object in accordance with the provided energy application characteristics, wherein, the temperature distribution estimating unit (5) is adapted for estimating a fourth temperature distribution in the second part of the object (3) within the second temperature range, which is present while the energy is applied to the object (3) in accordance with the provided applied energy application characteristics, if the first part of the object (3) has a temperature within the first temperature range and a second part of the object (3) has a temperature within the second temperature range, the fourth temperature distribution estimation being based on at least one of the measured volumetric first temperature distribution, the estimated second temperature distribution and the measured third temperature distribution.

8. The temperature distribution determining apparatus as defined in claim 1, wherein the temperature distribution determining apparatus comprises
   an energy application characteristics providing unit (4) for providing energy application characteristics describing the application of energy to the object (3) such that the object (3) is heated to a temperature within the second temperature range, and
   an energy application unit (20, 23) for applying the energy to the object (3) in accordance with the provided energy application characteristics.

9. The temperature distribution determining apparatus as defined in claim 1, wherein
   the temperature distribution measuring unit (6, 7) is adapted for measuring several sequential volumetric first temperature distributions in the object, while the energy is applied to the object (3) in accordance with several measurement energy application characteristics such that the object (3) is heated to different temperatures within the first temperature range,
   the temperature distribution determining apparatus comprises an energy application characteristics providing unit (4) for providing energy application characteristics describing the application of energy to the object (3) such that the object (3) is heated to a temperature within the second temperature range,
   the temperature distribution estimating unit (5) is adapted for estimating the second temperature distribution by extrapolating the several measured volumetric first temperature distributions from the several measurement energy application characteristics to the provided energy application characteristics.

10. The temperature distribution determining apparatus as defined in claim 1, wherein the temperature distribution determining apparatus (1) further comprises an object structure providing unit (13) for providing a structure of the object, wherein the temperature distribution estimating unit (5) is adapted to estimate the second temperature distribution based on the provided structure of the object.

11. The temperature distribution determining apparatus as defined in claim 1, wherein the temperature distribution determining apparatus (13) further comprises an influenced region determining unit (14) for determining an influenced region being indicative of the region of the object, in which the object has been influenced to a predefined degree by the application of energy.

12. A temperature distribution determining method for determining a temperature distribution within an object caused by applying energy to the object, the temperature distribution determining method comprising:
   measuring a spatially and temporally dependent volumetric first temperature distribution first temperature distribution in the object, while the energy is applied to the object such that the object is heated to a temperature within a first temperature range, by a temperature distribution measuring unit,
   estimating a spatially and temporally dependent second temperature distribution in the object within a second temperature range, which is different to the first temperature range and in which the temperature distribution measuring unit cannot measure a temperature distribution, based on a spatial and temporal extrapolation of the measured volumetric first temperature distribution,
   determining an estimated influence region of the object (3) depending on the estimated second temperature distribution, wherein the estimated influence region is indicative of the region of the object (3), in which the object (3) is influenced to a predefined degree by the application of energy, and displaying an overlay image of the estimated influence region and a predefined influence region.

13. A computer program product for determining a temperature distribution within an object caused by applying energy to the object, the computer program product comprising a non-transient computer-readable storage medium having encoded thereon:
   program code means for measuring a spatially and temporally dependent volumetric first temperature distribution in the object, while the energy is applied to the object such that the object is heated to a temperature within a first temperature range, by a temperature distribution measuring unit,
   program code means for estimating a spatially and temporally dependent second temperature distribution in the object within a second temperature range, which is different to the first temperature range and in which the temperature distribution measuring unit cannot measure a temperature distribution, based on a spatial and temporal extrapolation of the measured volumetric first temperature distribution,
   program code means for determining an estimated influence region of the object (3) depending on the estimated second temperature distribution, wherein the estimated influence region is indicative of the region of the object (3), in which the object (3) is influenced to a predefined degree by the application of energy, and
   program code means for displaying an overlay image of the estimated influence region and a predefined influence region.

* * * * *